(12) United States Patent
Kim

(10) Patent No.: US 6,267,597 B1
(45) Date of Patent: Jul. 31, 2001

(54) TOOTH RESTORATION USING FIBRE-REINFORCED COMPOSITE MATERIAL

(76) Inventor: Chang Yeal Kim, 4607 Vegas Road N.W., Calgary (CA), T3A 0M9

( * ) Notice: Subject to any disclaimer, the term of this patent is extended or adjusted under 35 U.S.C. 154(b) by 0 days.

(21) Appl. No.: 09/515,096

(22) Filed: Feb. 29, 2000

Related U.S. Application Data

(63) Continuation-in-part of application No. 09/055,143, filed on Apr. 3, 1998, now abandoned.

(51) Int. Cl.$^7$ ..................................................... A61C 5/02
(52) U.S. Cl. ......................................... 433/224; 433/220
(58) Field of Search ..................................... 433/220, 224

(56) References Cited

U.S. PATENT DOCUMENTS

| | | | |
|---|---|---|---|
| 4,104,798 | | 8/1978 | Takahashi et al. . |
| 4,894,012 | | 1/1990 | Goldberg et al. ..................... 433/215 |
| 4,936,776 | | 6/1990 | Kwistkowski ....................... 433/220 |
| 5,326,263 | * | 7/1994 | Weissman ............................ 433/220 |
| 5,328,372 | * | 7/1994 | Reynaud et al. ..................... 433/220 |
| 5,564,929 | | 10/1996 | Alpert ................................... 433/224 |
| 5,741,139 | | 4/1998 | Sicurelli et al. ..................... 433/220 |
| 5,797,748 | * | 8/1998 | Reynaud et al. ..................... 433/220 |
| 5,816,816 | * | 10/1998 | Scharf ................................... 433/224 |
| 5,861,445 | * | 1/1999 | Xu et al. ........................... 433/228.1 |
| 5,871,359 | * | 2/1999 | Billet et al. .......................... 433/220 |

OTHER PUBLICATIONS

"Shape and Color: the key to Successful Ceramic Restoration" by Gerald Ubasey, 1993, ISDN 0–8 6715–207–9 "Post and Core in Ceramics" pp179–183.
Canadian Dental Association brochure "Save that Tooth".
Sculpture/FibreKor Laboratory brochure "Non–Metal Encore Bridge With Sculpture/FibreKor Achieves Superior strength, Superb Esthetics" Oct. 1997.
Ivoclar Winter Edition 1995, article entitled "The Creation of All–Ceramic Restorations An Interview with M Gerald Ubassy" pp. 10–13 inclusive.
Ivoclar North America, Inc. brochure "Join the Esthetic Revolution" 1997.
The Sculpture/FibreKor System brochure "It's Simple".
Ivoclar North America, Inc. brochure "Natural to the Core".
Sculpture FibreKor brochures "Light as a Feather".
Sculpture FibreKor Instruction Manual booklet.
Ivoclar North America, Inc. brochure "Fascination of the Exceptional IPS Empress".
FibreKor Instruction Reference Manual issued by Jeneric/Pentrol Incorporated.
Ivoclar North America, Inc. in conjunction with Research and Development, manual "The Targis System"Dec. 1996.
"Evaluation of Cytotoxicity of Extracts of FibreKor Using the Agar Diffusion Method " paper written by Loma Linda Unversity of Dentistry–Feb. 14, 1997.
"Effect of Conquest Sculpture Composite Resin on Oral Mucous Membranes of Golden Syrian Hamsters" pape written by Indiana University of Dentistry–Oct. 23, 1996.
"A Fiber–Reinforced Polymer Bridge" paper written by M.A. Freilich, et al.
"Polymer–Based Conquest (Sculptur) Crown & Bridge Composite Material Properties According to ISO and ADA Standards/Specifications"–Report written by W. Jia et al. Jun. 1996.
"Performance of Fiber Reinforced Composites Intended for Prosthodontic Frameworks" written by Karmaker A.C. et al.

* cited by examiner

*Primary Examiner*—John J. Wilson

(57) ABSTRACT

A tooth restoration system for insertion into a tooth upon which root canal therapy has taken place. The system comprises a post, a core and a crown wherein the post is formed from a fibre-reinforced composite material and the core and crown are formed from a ceramic or a polymer/ceramic composite material. The fibre-reinforced composite material is molded to the root canal shape while still in a uncured or partially cured state so that it molds to the root canal. The post is then finally cured and the core and crown built up on the post to form the dental implant. The fibre-reinforced composite material comprises a polymeric matrix and a reinforcing fibre component embedded within the matrix.

5 Claims, 7 Drawing Sheets

TOOTH RESTORATION USING FIBRE-REINFORCED COMPOSITE MATERIAL

CROSS-REFERENCE TO RELATED APPLICATION

This application is a continuation-in-part of U.S. patent application Ser. No. 09/055,143 filed on Apr. 3, 1998, now abandoned.

FIELD OF THE INVENTION

The present invention relates to a tooth restoration system for restoring a tooth which has undergone root canal therapy.

BACKGROUND OF THE INVENTION

A human tooth comprises a crown and roots. The crown is the part of the tooth visible above the gumline while the roots are under the gums. The roots anchor the teeth to either the maxillary or mandibular bones. Within the roots are root canals which contain pulp. Pulp is live tissue which includes nerves and blood vessels.

The pulp may become infected and inflamed as a result of dental caries or physical trauma to the tooth. Endodontics is a branch of dentistry which treats teeth with diseased pulps. Endodontics is commonly referred to as root canal therapy. The goal of root canal therapy is to save the tooth by removing the diseased pulp. The root canal is then cleaned and filled. A crown or cap is typically placed on the tooth to protect the tooth and preserve its functionality.

In the prior art, porcelain fused metal ("PFM") systems are commonly used. In a conventional PFM system, a post and core are fashioned from one of a variety of suitable precious and non-precious metals. The post is made to snugly fit the root canal void and serves to anchor the core and crown. The core is built up onto the post and forms the support for the crown which replaces the injured tooth. The crown may be fashioned from porcelain (ceramic) material.

PFM systems enjoy excellent strength due to the metal post and excellent wear resistance due to the porcelain. However, a major drawback to PFM systems is the aesthetic appearance of the completed restoration. The enamel and dentin of a normal human tooth are slightly translucent which determines the natural look of a tooth. The metal post and core used in a PFM system reflects light passing through the artificial crown which results in the restoration looking unnatural.

A solution to this drawback of PFM systems is to replace the metal post with a ceramic material which simulates the translucency of normal teeth. An example is the Cosmo-Post™ system available from Ivoclar Vivadent, Ivoclar North America Inc. The post in this system is a zirconium oxide based ceramic, resulting in an aesthetically pleasing restoration. However, this system suffers from certain drawbacks. The posts are only available in preformed posts of a certain size and diameter. As a result, the dentist must perform the root canal therapy such that the root canal is the exact fit of the pre-formed post and to do so requires the use of proprietary root canal reamers.

Another solution to the aesthetic drawback of PFM systems is to use a carbon fibre based material such as the Composipost™ system available from Biodent of Quebec, Canada. This prior art system shares the same drawback as the CosmoPost™ system in that the posts are only available in preformed sizes and diameters. Again, special proprietary drills must be used in the canal preparation.

The root canal void created for using such prior art pre-formed posts are typically circular in cross-section as is shown in prior art FIG. 6A. As a result the dentist may not be able to remove all of the diseased pulp while retaining the necessary root canal void shape.

Posts are subject to high stresses once the restoration is complete and therefore the ceramic material used in the CosmoPost™ system and similar systems must be very strong. However, that strength prevents flexibility in fashioning the post. Other ceramic materials such as commonly available polymer/ceramic composites do not possess enough strength to be suitable material for root canal posts.

Therefore, it would be advantageous to have a tooth restoration system which combines the aesthetic qualities of an all-ceramic root canal restoration system with the strength of a conventional PFM system. It would be further advantageous for such a system to allow the convenient fabrication of a post which molds itself to the root canal and yet still possesses high structural strength.

SUMMARY OF THE INVENTION

In general terms, the invention in one aspect comprises a tooth restoration system for insertion into a tooth upon which root canal therapy has taken place, resulting in a root canal void having a certain shape; said system comprising a post, a core and a crown wherein:

(a) the post is formed from a fibre-reinforced composite material comprising a polymeric matrix and a reinforcing fibre component embedded within the matrix, said post having an upper end and a lower end wherein said lower end has previously been molded to the shape of the root canal void;

(b) the core is bonded to the upper end of the post and is formed from a ceramic material or a polymer/ceramic composite material; and (c) the crown is bonded to and partially surrounds the core and is formed from a ceramic material or a polymer/ceramic composite material.

In another aspect of the invention, the invention comprises a method of preparing a dental prosthesis comprising a post, a core and a crown for restoring a tooth upon which root canal therapy has taken place. In one embodiment the method comprises the steps of:

(a) creating a post from an uncured or partially cured fibre-reinforced composite material comprising a polymeric matrix and a reinforcing fibre component embedded within the matrix;

(b) molding a lower end of the post to fit the root canal void;

(c) curing the post;

(d) building up a core onto the upper end of the post from a ceramic or polymer/ceramic composite material; and (e) forming a crown around the core from a ceramic or polymer/ceramic composite material and shaping the crown to simulate the lost tooth.

The fibre reinforced composite material used in the present invention may comprise glass, carbon and/or graphite and polyaramid fibres. The polymeric matrix may include fully or partially polymerized thermoplastic materials. Suitable fibre reinforced composite materials are described in U.S. Pat. No. 4,894,012, although the present invention is not limited to those materials.

BRIEF DESCRIPTION OF THE DRAWINGS

The invention will now be described with reference to the following drawings in which.

DETAILED DESCRIPTION OF THE INVENTION

Figure 1:
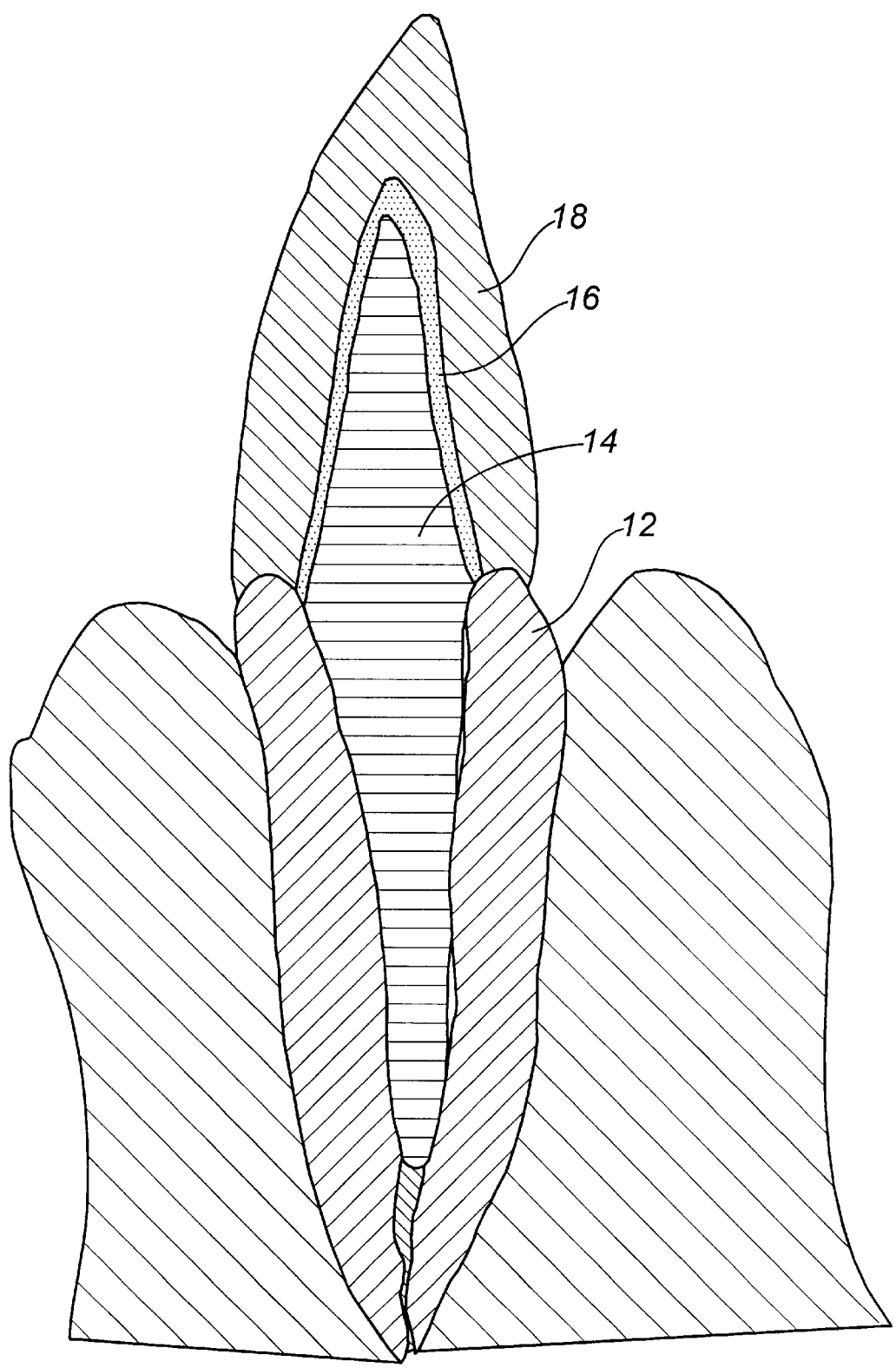
FIG. 1 is a cross-sectional view (distal/medial) of a tooth restored in accordance with the present invention.

The present invention provides for a system and method for preparing a dental prosthesis. The prosthesis comprises a post (14) which is made to fit the root canal void (10) after root canal therapy. The post (14) is used to support a core (16) and a crown (18). The post is made from a composite material comprising reinforcing fibres embedded in a polymeric matrix.

Suitable composite materials are commercially available. For example, Jeneric®/Pentron® Incorporated of Wallingford, Conn., USA manufactures and sells FibreKor™ in convenient ready-to-use sizes. Similarly, Ivoclar North America manufactures and sells Vectris™. Both FibreKor™ and Vectris™ are preferred composite materials for fabricating the post of the present invention. Once cured, they exhibit a high modulus of elasticity and high strength, matching that of non-precious alloys. They also exhibit translucency which closely matches that of human dental tissue, which is preferred for the present invention.

The composite material utilized in accordance with the present invention is composed of two essential components, a polymeric matrix and fibres embedded within the matrix. The fibers preferably take the form of long continuous filaments, although these filaments may be as short as 3 to 4 millimeters. Alternatively, shorter fibers of uniform or random lengths might also be employed.

Suitable composite material such as Fibre Kor™ or Vectris™ are available in a ready-to-use form. The material may be is packaged in small bundles of axially-oriented fibres impregnated with the polymeric matrix. The bundles are in a solid but flexible state. As a result, they may be manipulated and molded into a desired shape and will retain until fully cured, all in accordance with the present invention. Alternatively, the material may be packaged in other shapes, with varying degrees of fluidity that allow manipulations and shaping before curing.

Although a variety of fibers may be employed, the most commonly used fibers are glass, carbon and/or graphite, and polyaramid fibers such as the fibers sold under the trade name "Kevlar". Other materials such as polyesters, polyamides and other natural and synthetic materials compatible with the particular matrix also may be employed to provide selected properties.

The continuous filaments or fibers used in accordance with the present invention will vary in fiber diameter or denier as well as in fiber length, and it is preferred to utilize a range of fiber diameters. Where synthetic materials are employed, the diameters may vary from about 1.5 to 15 denier while for inorganic materials such as glass the fibers are usually very fine, with diameters falling in the low micrometer to submicrometer range. A typical range for glass fibers is about 0.3 to 25 micrometers with the preferred range being about 3 to 12 micrometers. Carbon and graphite fibers are typically near the low end of the range for glass and preferably exhibit diameters of about 3 to 12 micrometers. Those fibers may have an irregular cross section or may be circular or "dog-bone" in configuration.

In accordance with the present invention, it is preferred that a predominant number of fibers be aligned axially. The orientation results in some degree from the production techniques used to form the resultant product, but may also be specifically designed into these devices. These techniques include molding, such as compression molding, but the preferred technique is a form of extrusion known as pultrusion. In the pultrusion process, a sizing or coupling agent is applied to the continuous filaments to improve the wetting thereof by the polymeric matrix and enhance matrix fiber bond. The treated fibers are aligned and maintained in position as they are pulled through a bath of matrix polymer. The fibers are maintained under tension while the matrix material, which is in a near liquid state, ultimately engages and effectively wets the fibers and results in more effective coupling and hence improved mechanical properties. Physically holding the fibers in position helps to assure even and uniform distribution of the fibers in the final composite. As the fibers and matrix leave the polymer bath, the composite may pass through a series of rollers or dies to develop a uniform exterior or outside dimension and assure that the fibers do not protrude through the outside matrix surface.

The continuous fibers may be disposed in a parallel array relative to each other and may be aligned along one dimension such as the major dimension of the device being produced. The continuous filament composite material is capable of providing a material having a modulus of elasticity beyond the range available with polymeric materials used heretofore. For example, a continuous filament material can be formulated to provide a composite that exhibits a modulus in the range of 1.01 to $60 \times 10^6$ psi and greater. With glass or synthetic materials the modulus may be up to about $35 \times 10^6$ psi while with carbon fibers the modulus may fall within a range up to $40$–$50 \times 10^6$ psi.

The polymeric materials employed as the matrix for the reinforcing fibers preferably are fully polymerized thermoplastic materials although a wide variety of polymeric materials may be employed, including partially polymerized thermosetting materials. The thermoplastics allow ease of formability and the stiffness, strength, springback and creep resistance preferable for this invention. For example, the polymeric material may include polyamides such as nylon, polyesters, glycol esters such as polyethylene terephthalate glycol, polyolefins such as polypropylene or polyethylene, polyimides, polyarylates, polyurethanes, styrene, styrene acrylonitrils, ABS, polysufones, polyacetals, polycarbonates, polyphenylene sulfides, or a wide variety of other polymeric compositions including vinylesters and epoxy type materials. Among this group, the thermoplastic materials are preferred since they are not as brittle, exhibit greater toughness and more readily facilitate the formation of the post.

Figure 3:
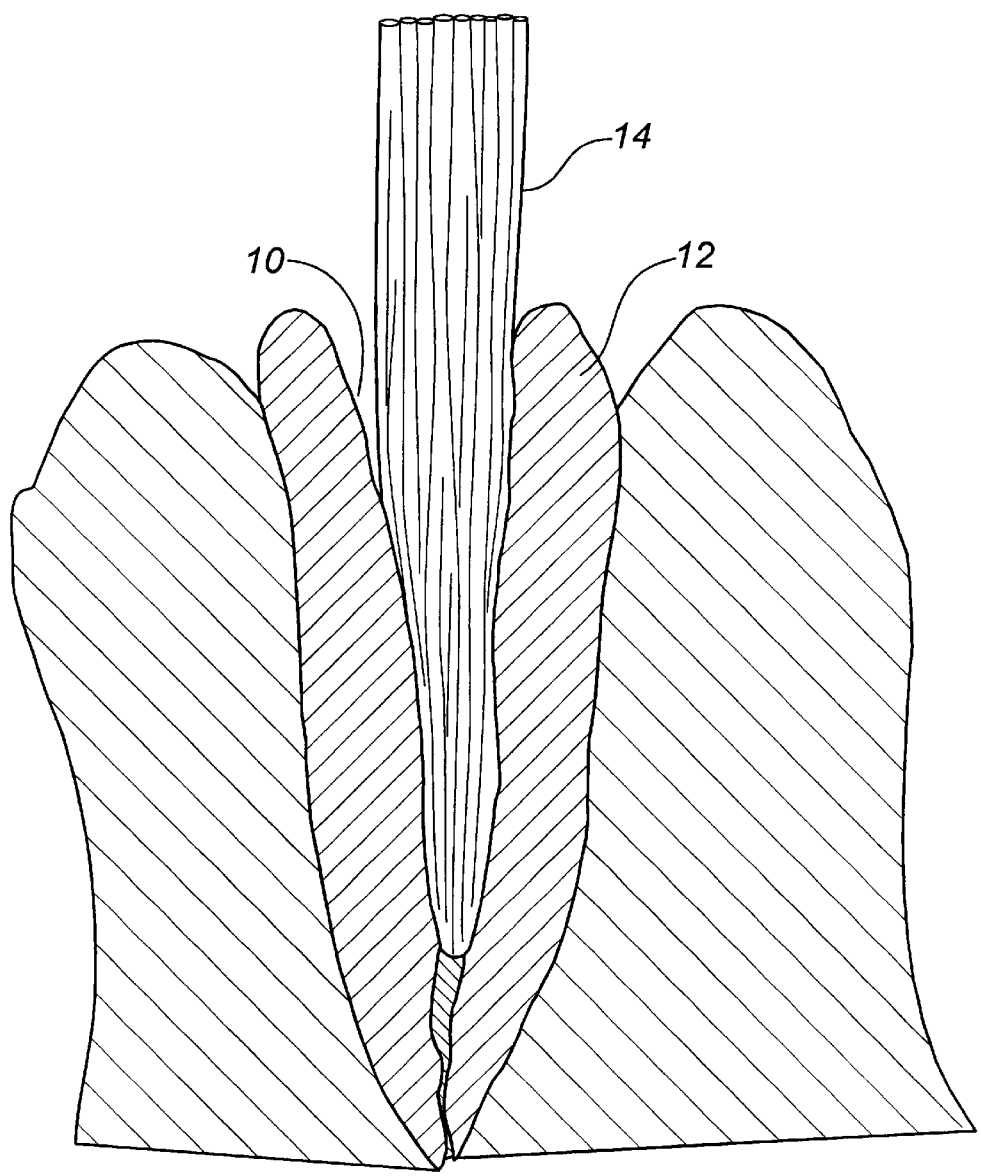
FIG. 3 is a cross-sectional view (labial) of the post before application of the core and crown.

The method of the present invention begins after root canal therapy has commenced and a mold is made of the root canal void (10) of the subject tooth (12) and the neighbouring teeth in a conventional manner. In one embodiment of the invention, the practitioner commences by determining the depth of the root canal void (10) and cutting a bundle (14) of the fibre-reinforced composite material to a length which will fill the void and protrude approximately 2 to 3 mm as shown in FIG. 3. The bundle may be created from pre-formed strips of the material and is used such that the orientation of the fibres runs up and down, substantially parallel to the root canal. The bundle should be formed to a diameter which snugly fits within the void (10) to ensure a proper fit in the tooth restoration. The bundle should be tamped down slightly within the root canal so as to better mold it to the root canal. At all times, the material is not handled by hand so as to avoid contamination, in accordance with the manufacturer's instructions.

It is essential that the bundle be uncured or only partially cured when it is first formed. Because the bundle is flexible before curing, the bundle will mold itself to the shape of the root canal void (10) to ensure a proper fit as is shown in the Figures. Once a proper bundle is created, the bundle may then be cured to complete polymerization of the matrix material. It is preferable to use light-curing material although other curing methods are available and may be suitably adapted to the present method.

In another embodiment of the invention, the method may be modified to allow use of a more fluid fibre reinforced composite material and to use a vacuum assisted curing process. In this embodiment, the mold of the root canal void is filled with wax which is molded to approximate the shape of the intended shape of the post (14). Then, a kneadable silicone compound is used to form a secondary mold or "index" around the wax. The wax may then be removed and the mold and index filled with the composite material. This combination may then be inserted into a light curing/vacuum unit such as a Vectris® VS 1 unit. In a machine such as this, a membrane is placed over the mold and index and a vacuum applied underneath the membrane, while the composite material is light cured. The application of a vacuum during the curing process may increase the strength of the cured product by reducing air bubbles present in the composite material. Without the additional support of the index, the application of the vacuum to the membrane may cause the shape of the post to distort during the curing process. After curing, the index may be removed and the post (14) is now ready for application of the core (16) and the crown (18).

Figure 2:
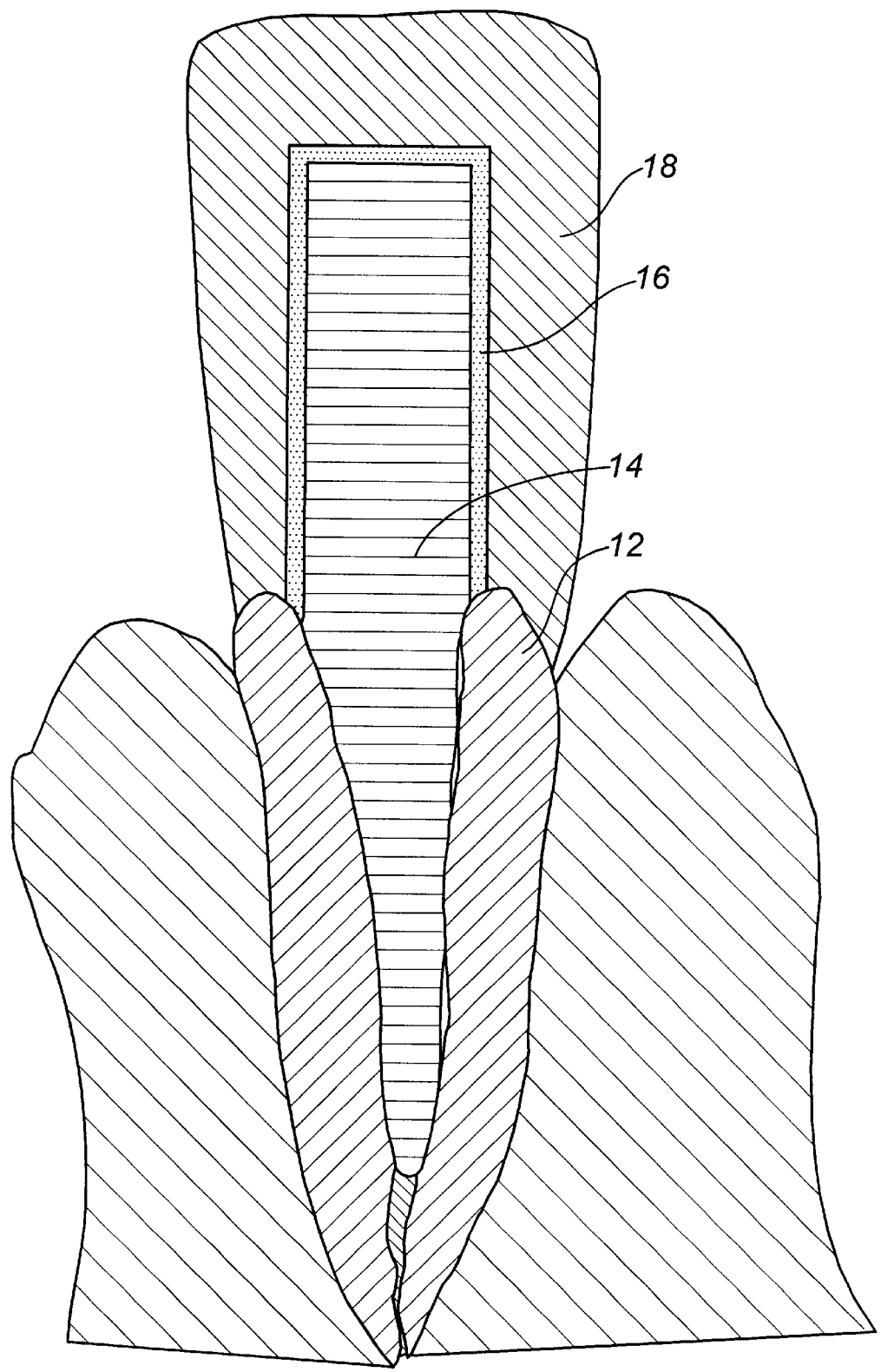
FIG. 2 is a cross-sectional view (labial) of a tooth restored in accordance with the present invention.
Figure 4:
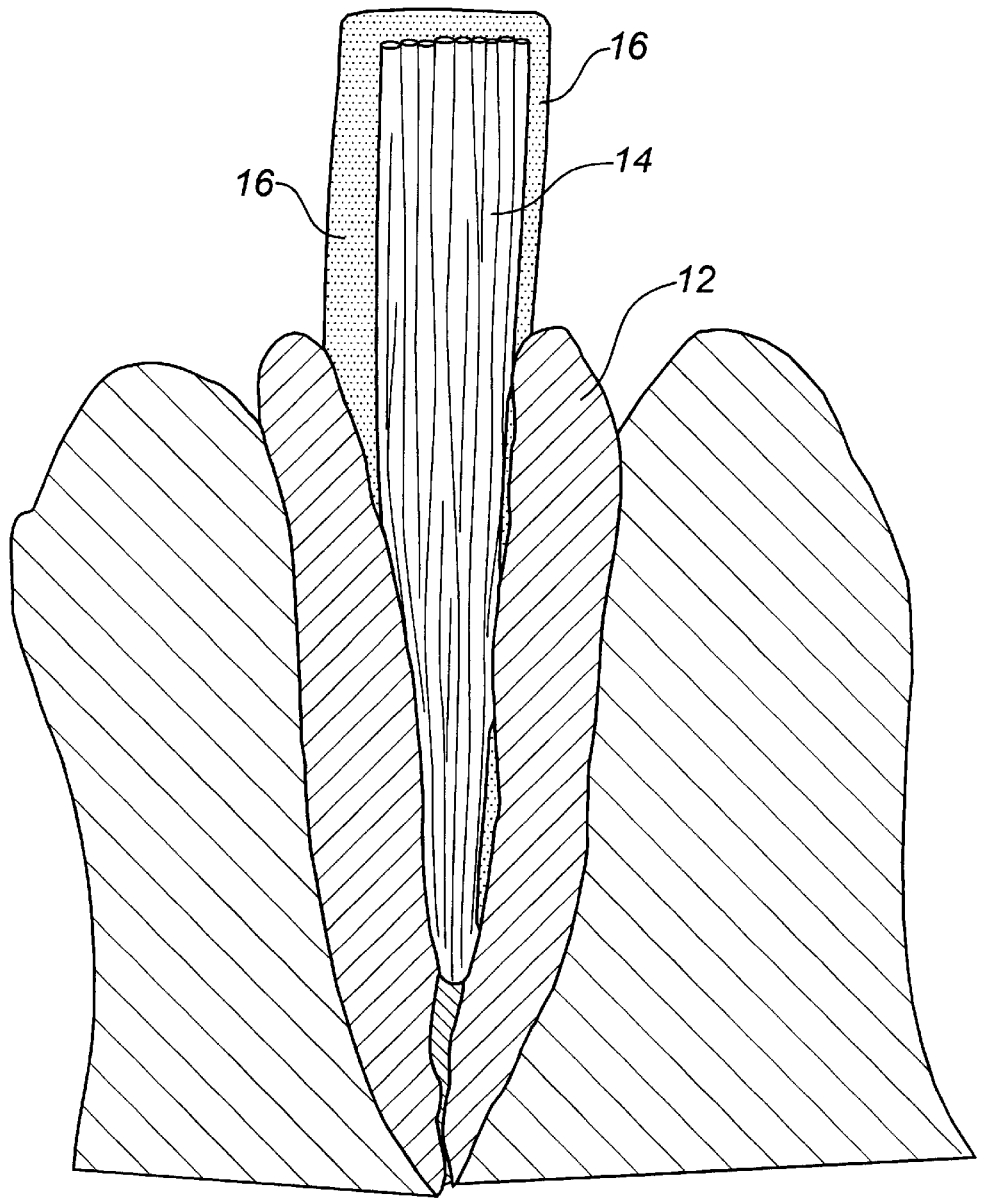
FIG. 4 is a view of the formed post with the core applied.
Figure 5:
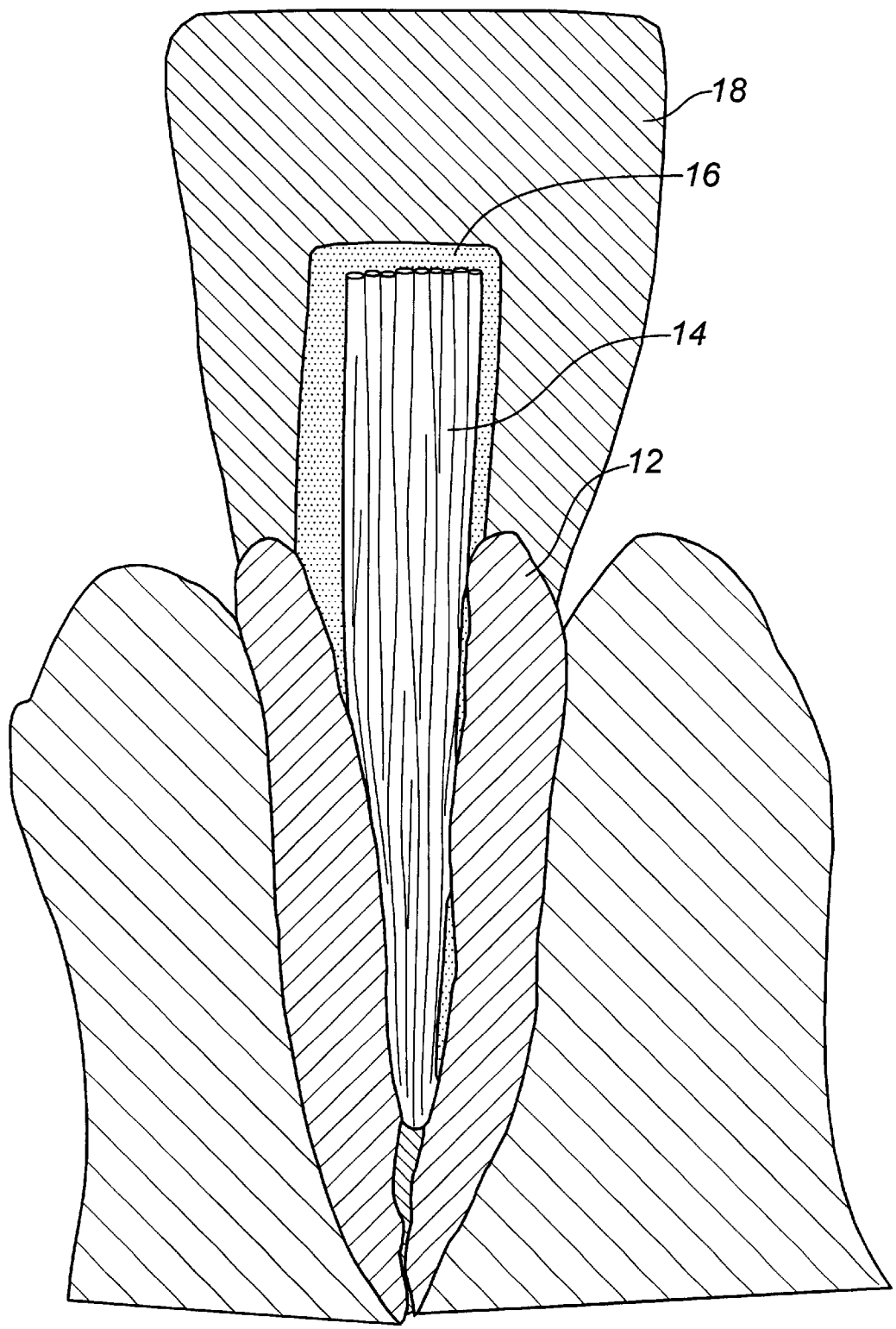
FIG. 5 is a view of the post, core and crown combination.
Figure 6A:
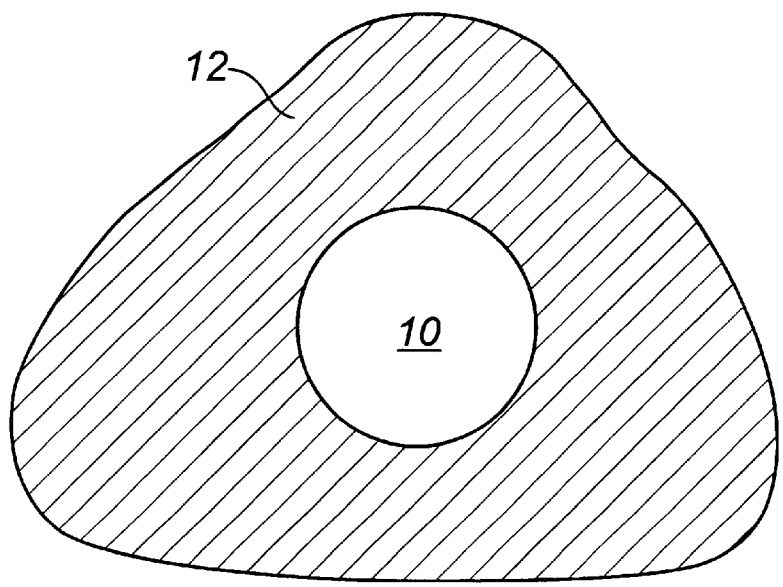
FIG. 6A is a similar view of a root canal void necessary for installing a prior art post.
Figure 6:
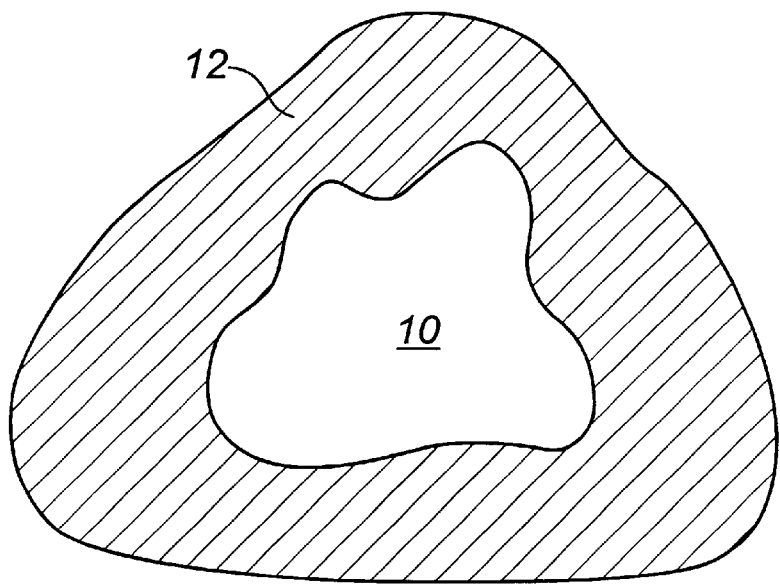
FIG. 6 is a cross-sectional view (occlusion/incisal) of a root canal void prior to molding a post to fit the void space.
Figure 7:
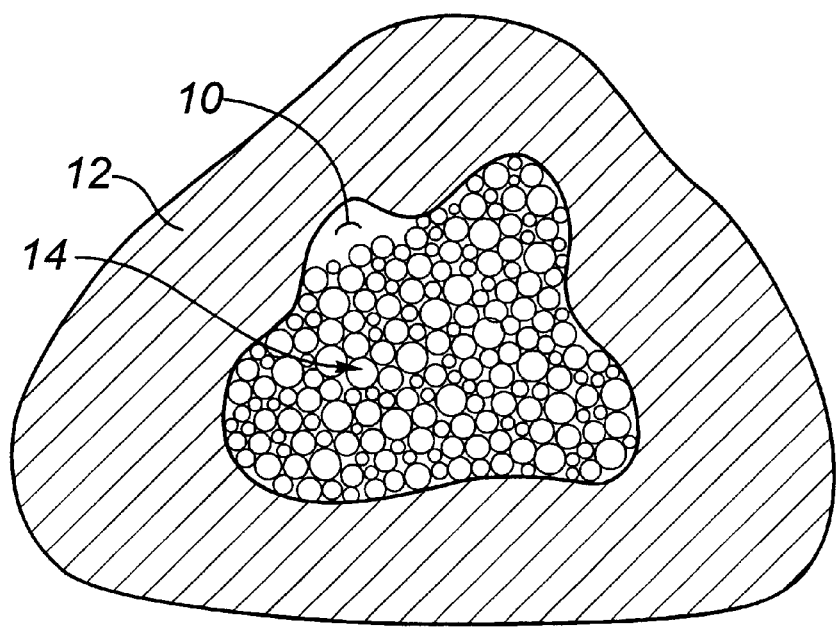
FIG. 7 is the cross-sectional view of FIG. 6 showing insertion of a molded post.

Upon curing, the bundle (14) becomes the post (14). The core (16) and the crown (18) are then built up onto the post (14) using conventional and well-known techniques and materials as is shown in FIG. 4 and 5. Preferred materials for the core and crown include polymer/ceramic composite materials such as Sculpture™ available from Jeneric®/Pentron® Incorporated or Targis™ available from Ivoclar North America. The completed post/core/crown combination may then be installed in the root canal using conventional and well known techniques and adhesives. FIGS. 1 and 2 show a completed restoration.

As will be apparent to those skilled in the art, various modifications, adaptations and variations of the foregoing specific disclosure can be made without departing from the teachings of the present invention.

The embodiments of the invention in which an exclusive property or privilege is claimed are defined as follows:

1. A method of preparing a dental prosthesis comprising a post, a core and a crown for restoring a tooth upon which root canal therapy has taken place, the method comprising the steps of:

(a) creating a post from an uncured or partially cured fibre-reinforced composite material comprising a polymeric matrix and a reinforcing fibre component embedded within the matrix;

(b) molding a lower end of the post to fit the root canal void;

(c) curing the post;

(d) forming a core onto the upper end of the post from a ceramic or polymer/ceramic composite material; and (e) forming a crown around the core from a ceramic or polymer/ceramic composite material and shaping the crown to simulate the lost tooth.

2. The method of claim 1 wherein the fibre-reinforced composite material is similarly translucent to human dental tissue.

3. The method of claim 2 further comprising the step of inserting and securing the dental prosthesis into the root canal void.

4. The method of claim 1 wherein the post is cured while a vacuum is applied to the post.

5. A method of preparing a dental prosthesis comprising a post, a core and a crown for restoring a tooth upon which root canal therapy has taken place, the method comprising the steps of:

(a) creating a mold of the tooth upon which root canal therapy has taken place;

(b) creating a temporary post approximating the shape of the intended post;

(c) creating an index around the temporary post;

(d) removing the temporary post and filling the mold with an uncured or partially cured fibre reinforced composite material comprising a polymeric matrix and a reinforcing fibre component embedded within the matrix;

(e) curing the post while applying a vacuum;

(f) forming a core onto the upper end of the post from a ceramic or polymer/ceramic composite material; and (g) forming a crown around the core from a ceramic or polymer/ceramic composite material and shaping the crown to simulate the lost tooth.

* * * * *